United States Patent [19]

Fixel

[11] 4,432,358

[45] Feb. 21, 1984

[54] COMPRESSION HIP SCREW APPARATUS

[76] Inventor: Irving E. Fixel, 111 N. 31st Ave., Hollywood, Fla. 33021

[21] Appl. No.: 341,863

[22] Filed: Jan. 22, 1982

[51] Int. Cl.³ .............................................. A61F 5/04
[52] U.S. Cl. ............................ 128/92 BB; 128/92 D; 128/92 B
[58] Field of Search ............ 128/92 BB, 92 B, 92 BA, 128/92 D

[56] References Cited

U.S. PATENT DOCUMENTS 3,029,811  4/1962  Yost ............................... 128/92 BA
3,374,786  3/1968  Callender ...................... 128/92 BB Primary Examiner—Richard J. Apley
Assistant Examiner—David J. Isabella
Attorney, Agent, or Firm—Richard M. Saccocio

[57] ABSTRACT

Compression hip screw apparatus comprising a lag screw, a hip plate, a compression nut and a locking assembly. The lag screw is inserted through the barrel of the hip plate after the hip plate is installed which eliminates the need to find a lag screw buried within the femur. Keyless construction further aids assembly. The locking assembly frictionally locks together the lag screw, the hip plate and the compression nut.

8 Claims, 2 Drawing Figures

U.S. Patent     Feb. 21, 1984     4,432,358
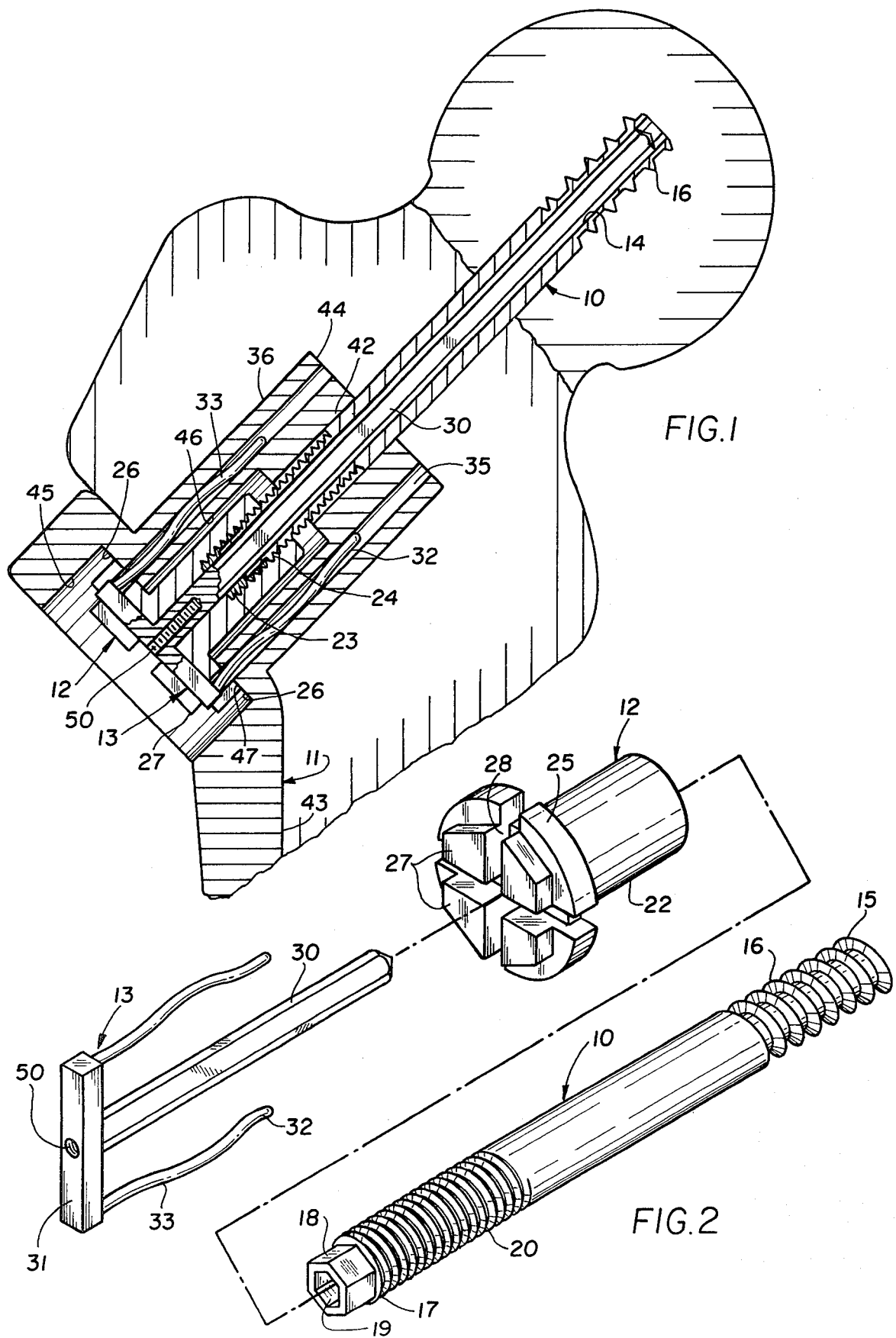

COMPRESSION HIP SCREW APPARATUS

BACKGROUND OF THE INVENTION

1. Field of the Invention

This invention relates in general to the field of implanted bone fixation devices and in particular to a device for operative reduction and internal fixation of femoral head, neck or intertrochanteric fractures.

2. Description of the Prior Art

Fractures across the head, neck or intertrochanter of the femur whereby the broken portion is separated from the femur are fairly common especially in older people. Any person having a minimal knowledge of the hip bones and joint is well aware of the significance of such a fracture. The peculiar configuration of the femur at the hip joint in conjunction with the severity of the cyclic loads imposed at the hip joint during normal activities such as walking leads one to wonder how a femoral break at the hip joint can ever be successfully repaired through surgery. Fortunately, the success of surgical reduction and fixation is fairly high due, in part, to the availability of some excellent internal fixation devices, one of which is commonly known as a compression hip screw, and advanced modern day surgical techniques. Indeed, it is not uncommon for a patient to begin walking almost immediately following an operation involving internal fixation of the femur at the hip joint.

This is not, however, to imply or suggest that one hundred percent success is continually attained. Nor is it suggested that present-day compression hip screws do not fail. And, it is not suggested that the present day compression hip screws assure success of bone reduction and fixation. Although many factors are involved, such as the nature of the break, the healing capabilities of the patient, the expertise of the operating surgeon, etc., some failures are attributable to the compression hip screw itself because of the many conflicting requirements imposed on such devices.

Basic components of a compression hip screw include a lag screw, a barrel hip screw plate and a compressing screw. The lag screw comprises a long shaft having lag threads on one end. The lag screw extends across the break and into the femoral head. It is used to reduce the fracture and permit impaction of any fragments. The barrel hip plate engages the free end of the lag screw and extends down and is secured to the lateral side of the femur. The lag screw and the plate are generally at an inclined angle of 135° or more, relative to each other. The compressing screw connects the lag screw to the plate and allows for compression (reduction) of the fracture.

It is highly desirable that the lag screw remain rotationally fixed relative to the plate in order to assure that the broken fragment does not rotate relative to the femur. A key and keyway arrangement between the lag screw and the barrel of the plate is one way the prior art compression hip screws prevent such relative rotation. However, because the lag screw is buried within the trochanter, the neck and the head of the femur during surgery, it is extremely difficult for the operating surgeon to "find" the shaft of the lag screw for its fit up with the barrel on the plate. Finding the keyway on the shaft is even more difficult. Once key and keyway are mated, the problem is not solved. There is a high probability that the plate is then not axially aligned with its mating surface along the length of the femur. This necessitates removal of the plate, rotation of the lag screw, and then reinsertion of the plate. This procedure may be required to be repeated a number of times until alignment is achieved. Each time, the free end of the lag screw must be located and the key-keyway fit up accomplished. This is obviously not a satisfactory procedure.

The difficult nature of the above-stated problem has led to the development of and use of the "keyless" compression screw. As the name implies, no mating key-keyway arrangement is used for the lag screw-barrel fit up. Without a doubt, this keyless arrangement eliminates the above-described alignment problem, but in so doing, it provides no assurance that the femoral head will not rotate relative to the femur (or the lag screw relative to the hip screw plate) during the operation or during the postoperative period of bony healing.

In other words, the "keyless" solution simply ignores relative rotation problems. The adverse consequences of relative rotation including femoral head rotation which in addition to patient discomfort, may include delayed healing or nonunion of the bone and appliance bending, breaking or pull out from the bone. Obviously, not a satisfactory result, indicating that relative rotation should not be ignored.

Another troublesome aspect of the prior art compression hip screws is the necessity of the lag screw to slide relative to the barrel of the plate during surgery and during postoperative healing and union of the bone. To attain proper reduction of the break and proper impaction of the broken fragments, the lag screw must slide within the barrel portion of the hip screw plate. A key-keyway arrangement, even if accurately aligned, inhibits sliding and therefore hampers proper reduction and impaction. Bone absorption during the post-operative period also requires sliding between the barrel and lag screw. Again, the key-keyway arrangement opposes such movement. The keyless compression screw on the other hand, allows such relative sliding, but as stated above, it has certain disadvantages of its own.

Accordingly, it is a primary object of the present invention to provide an internal hip fixation device for fractures of the proximal portion of the femur which is keyless and therefore easy to install but prevents relative rotation between the lag screw and the barrel of the hip screw plate and the compressing screw.

SUMMARY OF THE INVENTION

The inventive implant is adapted to be applied to a femur having one or more breaks across the proximal end thereof. The invention comprises a lag screw, a compression nut, a hip plate, and a locking pin assembly.

The lag screw comprises an elongated hollow bar having self-tapping lag screw threads at one end thereof and external machine screw threads with a hexagonal internal configuration at the other end. The hip plate comprises an elongated plate for attachment to the shaft of the femur with a barrel portion extending therefrom at an obtuse angle. The barrel portion has a smooth bore therethrough.

The compression nut includes internal machine screw threads connecting the lag screw to the hip plate and compressing together the broken portions of the femur. A hexagonal projection allows the compression nut to be driven onto the lag screw. The locking pin assembly comprises a three-pronged pin which simultaneously locks the compression nut to the barrel of the hip plate and the barrel to the lag screw.

Because of the unique configuration of the various components, the instant invention allows for the simplicity of installation of a keyless assembly but prevents relative rotation of the femoral head during and after surgery.

BRIEF DESCRIPTION OF THE DRAWINGS

The above specifically noted advantages and objects in addition to others not specifically mentioned will be further apparent from a consideration of the following accompanying drawings together with the following description of the specific embodiments in which:

FIG. 1 is a cross-sectional view of the inventive implant as applied to the proximal end of a femur having a break across the neck thereof; and, FIG. 2 is an expanded isometric view of the lag screw, compression nut and locking pin of the inventive implant.

DESCRIPTION OF THE PREFERRED EMBODIMENTS

Referring now to the drawings, FIG. 1 depicts the inventive implant, in cross section, as applied to a femur having a break across the neck thereof. In general, the implant comprises a lag screw 10, a hip plate 11, a compression nut 12, and a locking pin assembly 13.

Lag screw 10 comprises an elongated hollow or cannulated bar having a generally circular cross-sectional shape. The cannulated feature 14, as in the prior art, allows the screw 10 to be guided, during insertion, by a guide wire (not shown) which is positioned within a hole drilled in the femur, across the break and into the head.

FIG. 2 shows the lag screw 10 separate and apart from the remainder of the components of the implant. A first end 15 of lag screw 10 includes self-tapping lag screw threads 16 as are commonly known in the prior art and which have been shown to be most effective. A second end 17 of lag screw 10 includes an external hexagonally-shaped portion 18 which serves the purpose of allowing lag screw 10 to be fitted to an appropriate tee-handled socket wrench (not shown) for insertion of lag screw 10. Of course, any appropriate shape, suitable for driving lag screw 10 during insertion of the same, may be used on end 17 as an alternative. End 17 of lag screw 10 is also provided with an internal opening having a hexagonal cross section 19 for purposes which will become apparent hereinafter. End 17 is further provided with external screw threads 20 for purposes of mating with compression nut 12.

Compression nut 12 includes a cylindrical body 22 which is bored 23 and threaded 24 to mate with threads 20 on lag screw 10. As shown, bore 23 is not a through hole; however, a through hole would equally suffice. A head 25 limits the insertion of nut 12 within hip plate 11 and shoulders against surface 26 of hip plate 11. A hexagonally-shaped projection 27 extends from head 25 allowing nut 12 to be driven onto lag screw 10 by an appropriate wrench. One or more cross slots 28 are provided within head 25 and hexagonal projection 27 for purposes of permitting locking pin assembly 13 to be fitted thereto and therethrough.

Locking pin assembly 13 comprises a hexagonally-shaped center bar 30, a cross bar 31 positioned at right angles to center bar 30, and at least one locking pin 32. Locking pin 32 is substantially parallel to but shorter than center bar 30 and spaced therefrom by cross bar 31. Locking pin 32 may comprise an elongated bar, circular in cross section, which includes one or more warped or bent portions 33. Locking pin 32 is preferably made from spring stainless steel. Locking pin 32 fits within a hole 35 provided in barrel portion 36 of hip plate 11. Hexagonally-shaped center bar 30 fits within hexagonal opening 19 of lag screw 10 and may substantially extend the full length of lag screw 10 (FIG. 1) adding strength thereto which was removed by the cannulation. Cross bar 31 fits within one of the cross slots 28 provided within compression nut 12 while locking pin 32 fits therethrough. Hence, locking pin assembly 13 simultaneously locks together lag screw 10, hip plate 11, and compression nut 12.

The amount of warp 33 placed in locking pin 32 is determinative of the friction-locking force and is dependent in part upon the diameter of locking pin 32, the length of locking pin 32, the diameter of opening 35, the length of the warp, the number of warps as well as the type of material locking pin 32 is made from. For example, if the diameter of hole 35 is only slightly larger than the diameter of pin 32, then a slight amount of warp will produce a high locking force. If the diameter of pin 32 is large relative to the length of the warp, a high locking force is again achieved. The height of the warp (perpendicular displacement from the longitudinal axis of pin 32) relative to the other above-stated features also determines the amount of locking force. A preferred amount of locking force is that amount which would prevent locking pin assembly 13 from being withdrawn as a result of normal physical activities of a patient having the implant, yet not so much as to prevent the assembly 13 from being purposely withdrawn by an operating surgeon. Hole 50 in cross bar 31, which may be threaded, is provided to allow an operating surgeon to remove locking pin assembly 13 with the aid of an appropriate extraction tool (not shown).

Hip plate 11 includes a circular opening 42 which is slightly larger than the outer diameter of lag screw 10. Opening 42 serves to accurately locate and fix the position of lag screw 10. Hip plate 11 may be secured to the lateral side of the femur by means of screws which are well known in the art.

The following comprises a general description of a technique which may be used to apply the inventive implant, and to further explain and describe the inventive implant.

A guide wire (not shown) is inserted in normal fashion at a point below the flare of the greater trochanter through the neck of the femur and into the femoral head. The location of the guide wire is then checked by A/P and lateral x-rays. A combination reamer is used in conjunction with the guide wire to prepare a hole having concentric diameters of the lag screw 10 and the barrel 36 of hip plate 11. Care should be taken to drill the concentric diameter holes to a proper predetermined depth. The next step is to drill and tap the lag screw threads 16. This may be accomplished by means of a special tool having the combined shape of the lag screw 10 and the barrel 36 or by using the self-cutting threads 16 of lag screw 10 in combination with an attachment duplicating the size and shape of barrel 36. In either event, it is preferable that a length be tapped slightly shorter than the length of the threads 16 of lag screw 10 to allow an operating surgeon to fix the final insertion of lag screw 10 during the insertion of the same.

Upon drilling the hole for barrel 36 and the hole and threads for lag screw 10, hip plate 11 is fitted to the lateral side of the femur with barrel 36 being inserted within the hole prepared in the femur. The elongated portion 43 of hip plate 11 is then attached to the lateral side of the femur and secured thereto by bone screws (not shown). Lag screw 10 is inserted within the through hole 42 in barrel 36. The close fit between hole 42 and the outer diameter of lag screw 10 serves the purpose of guiding lag screw 10 during the insertion step. If desired, the guide wire may also be used during this step. Lag screw 10 will therefore be precisely guided within the hole prepared in the neck and the head of the femur. Lag screw 10 may be inserted through barrel 36 after hip plate 11 is secured to the femur because the outer diameter of threads 16 is equal to or slightly smaller than the diameter of the shank of lag screw 10. In the alternative, if it is desired to utilize larger lag screw threads (having a diameter greater than the outer diameter of the shank of lag screw 10), end 17 of lag screw 10 may be inserted through and into hole 42 in barrel 36 from end 44 of barrel 36, then hip plate 11 is applied to and is secured to the femur. In either event, a wrench is then fitted to the hexagonal portion 18 of end 17 of lag screw 10 and lag screw 10 is threaded and seated into the threaded hole previously prepared in the head of the femur. In this manner, there is no need to find end 17 of lag screw 10 with end 44 of barrel 36.

Compression nut 12 is next inserted within counterbores 45 and 46 of hip plate 11 and onto the threads 20 of end 17 of lag screw 10. The hexagonal projection 27 which may be fitted to an appropriate socket wrench may be utilized to facilitate this step. Compression nut 12 is increasingly engaged onto threads 20 until surface 47 of head 25 seats against surface 26 of counterbore 45. Further rotation of nut 12 causes reduction of the fracture and impaction of any bone fragments. When sufficient reduction is attained, nut 12 is further rotated to cause alignment of the closest slot 28 with one of holes 35 in the barrel 36 of the hip plate 11.

The next step is to insert locking pin assembly 13. This is accomplished by partially inserting center bar 30 (which is longer than locking pin 32) within the hexagonal hole 19 in lag screw 10 to determine if locking pin 32 is properly aligned with slot 28 and hole 35. If such alignment does not exist, lag screw 10 may be further rotated independent of compression nut 13 by rotating locking pin assembly 13. The fit up between hexagonal center bar and hexagonal hole 19 allows such rotation to be accomplished. Rotation is continued until locking pin 32 is aligned with slot 28 and hole 35, at which point locking pin assembly 13 is fully inserted as shown in FIG. 1. Since pins 32 are warped as previously described, a slight amount of pushing force is necessary to fully insert locking pin assembly 13. After assembly is complete, this same force then serves to lock the implant together as a single unit and prevent compression nut 12 from unthreading or becoming loose from normal use of the hip following the surgery.

Threaded hole 50 in the end of center bar 31 allows the operating surgeon to remove the locking pin assembly 13 either during or after the surgery. This may be accomplished by utilizing an appropriate tool to engage the threads of hole 50 and applying the necessary removal force.

While the invention has been described, disclosed, illustrated and shown in certain terms or certain embodiments or modifications which is has assumed in practice, the scope of the invention is not intended to be nor should it be deemed to be limited thereby and such other modifications or embodiments as may be suggested by the teachings herein are particularly reserved especially as they fall within the breadth and scope of the claims here appended.

I claim:

1. Compression hip screw apparatus adapted for internal fixation and compression of a fractured portion of the proximal femur comprising
    plate and barrel means for attaching said apparatus to said femur wherein said barrel means includes a smooth bore therethrough;
    screw means for internally fixing the fractured portion of said femur, said screw means including a smooth cylindrical outer surface which is slidingly received within said smooth bore in said plate and barrel means;
    compressing means for compressing said fractured portion to said femur, said compressing means being adjustably attached to an end of said screw means; and,
    locking means for simultaneously locking together said plate and barrel means, said compressing means, and said screw means.

2. The apparatus of claim 1, wherein said plate and barrel means includes an elongated plate having a substantially right circular cylindrical barrel member angularly attached to an end thereof, said smooth bore in said barrel being counterbored from the plate end thereof.

3. The apparatus of claim 2, wherein said screw means comprises an elongated rod having screw threads at each end thereof with a first end fitting closely within said bore of said barrel and a second end internally fixed to said fractured portion of said femur.

4. The apparatus of claim 3 wherein said compressing means comprises a ring member having internal screw threads attached to said first end of said screw means and seated against the planar surface of said counterbore.

5. The apparatus of claim 1, wherein said locking means comprises a first elongated member receivingly fitted within an opening in said screw means, a second elongated member attached to said first elongated member and receivingly fitted within an opening in said compressing means and means for connecting said compressing means to said plate and barrel means.

6. The apparatus of claim 5, wherein said means for connecting said compressing means to said plate and barrel means comprises a third elongated member attached to said second member including means for frictionally attaching said locking means to said plate and barrel means.

7. The apparatus of claim 6, wherein said frictional attaching means comprising at least one curve in said third elongated member along the longitudinal axis thereof.

8. The apparatus of claim 7, wherein said first elongated member is longer than said third elongated member whereby said first elongated member may be engaged with said screw means when said third elongated member is disengaged from said plate and barrel means.

* * * * *